United States Patent [19]
Kater

[11] 3,993,049
[45] Nov. 23, 1976

[54] ELECTRODES AND MATERIALS THEREFOR

[76] Inventor: John A. R. Kater, 583 Traverse Drive, Costa Mesa, Calif. 92626

[22] Filed: Dec. 26, 1974

[21] Appl. No.: 536,335

[52] U.S. Cl. .......................... 128/2.06 E; 128/2.1 E; 128/417; 128/DIG. 4
[51] Int. Cl.² .......................................... A61B 5/04
[58] Field of Search ....... 128/2.06 E, 2.1 E, DIG. 4, 128/417, 418, 404

[56] References Cited
UNITED STATES PATENTS

| | | | |
|---|---|---|---|
| 2,055,540 | 9/1936 | Karnofsky | 128/417 |
| 3,518,984 | 7/1970 | Mason | 128/2.06 E |
| 3,528,408 | 9/1970 | Opperman | 128/2.1 E |
| 3,547,105 | 12/1970 | Paine | 128/2.06 E |
| 3,565,059 | 2/1971 | Hauser | 128/2.06 E |
| 3,607,788 | 9/1971 | Adolph | 128/418 |
| 3,636,043 | 1/1972 | Magerlein | 128/417 A |
| 3,665,064 | 5/1972 | Mosier | 128/2.1 E |
| 3,710,782 | 1/1973 | Hauser | 128/2.06 E |
| 3,750,094 | 7/1973 | Zenkich | 128/2.06 E |
| 3,828,766 | 8/1974 | Knasnow | 128/2.1 E |
| 3,834,373 | 9/1974 | Sato | 128/2.06 E |
| 3,911,906 | 10/1975 | Reinhold, Jr. | 128/2.06 E |

FOREIGN PATENTS OR APPLICATIONS 1,965,195   7/1971   Germany ...................... 128/2.06 E Primary Examiner—Robert W. Michell
Assistant Examiner—Lee S. Cohen
Attorney, Agent, or Firm—Grover A. Frater

[57] ABSTRACT

An electrolyte for a bio-electric event measuring electrode combines a salt with adhesive. The adhesive serves as the vehicle for dispersing solvent to form the electrolyte in a solid or semi-solid mixture. The adhesive serves further as a structural element in holding the parts of a practical electrode together and in making the electrode adhere to a subject's skin.

Such an electrolyte is combined with a mesh or otherwise foraminated patch of pliant material and a connector to form what can be an inexpensive, effective electrode having long shelf life, low irritation, and low electrical resistivity.

14 Claims, 6 Drawing Figures

ELECTRODES AND MATERIALS THEREFOR

This invention relates to improvements in electordes for use in measuring bio-electric events and to compositions for use in such electrodes.

The magnitudes of the electric potentials that characterize such events are very small. Contact potentials which result from ionic activity at liquid-to-liquid and liquid-to-metal and metal-to-metal interfaces may have the same order of magnitude as bioelectric potentials. Moreover, junction potentials are not uniform. They vary with micro changes in ion concentration that results from other than the event of interest. Such variations in junction potentials are called "artifacts," and if they are occasioned by relative motion between the elements that constitute a measuring circuit as an incident to motion of the subject, or otherwise, they are called "motion artifacts."

It is possible to minimize junction potentials and motion artifacts, and to arrange circuits in which junction potentials are closely predictable, by proper selection of the circuit materials and the attaching elements. In particular, the materials at interfaces between dissimilar materials are selected so that ion exchange proceeds reversably. Junctions of that kind are called non-polarizing junctions, and the materials which provide best results are well known.

However, the problem of providing a suitable electrode for application to skin cannot be optimized by electro-chemical considerations alone. The cardiac patient whose heart action must be monitored and who must wear electrodes for protracted periods, astronauts who must wear electrodes for many days, are all concerned with the irritation which those electrodes produce. More than discomfort is involved. The skin may be damaged and discolored.

It is possible to optimize the electro-chemical action and construction of an electrode while minimizing the possibility of electrical motion artifacts. That can be accomplished to some degree by an electrode which includes a sponge soaked with electrolyte. The sponge is carried in a cup and has a silver coated stud overlying the sponge. That arrangement is used in a commercially available electrode. It requires a relatively heavy salt concentration in the electrolyte to reduce the resistivity of the junction to an acceptable value and it requires a large area of adhesive to retain the cup and sponge in contact with the skin. That construction may solve much of the motion artifact problem, but the necessarily heavy salt concentration results in undue irritation. It is one of the objects of this invention to provide an electrode which permits use of the materials which provide the best available electrochemical behaviour, which is equal or better than prior constructions in minimizing the generation of motion artifact potentials, and which is free from irritation and discomfort in a degree previously unknown in practical electrodes.

Another object of the invention is to provide an electrode which has long shelf life and is easily and inexpensively manufactured. The days are gone, or should be, when the electro-cardiograph and encephalograph technician smeared gel on the patient's body and strapped down or taped on a metal button or plate. Modern procedures and cleanliness standards, and the need for optimum performance equipment dictate that electrodes not be reused. A fresh electrode is used in each instance. Thus, electrodes are required to be disposable and that term implies an electrode that is packaged in sterile, ready-to-use condition. If possible, the disposable product should be inexpensive. All of those objectives are accomplished in the invention. Another object is to provide a disposable electrode that meets those requirements.

Some disposable electrodes require the addition of electrolyte in liquid or gel form immediately prior to use. Others may be impregnated with, or carry the electrolyte, in liquid or gel form. But that kind often must be specially handled to prevent squeezing out of the electrolyte material, and in general, has the difficulty that shelf life is relatively short. An object of the invention is to provide an electrode, the electrolyte in which is a solid or semi-solid, which does not require special handling, which can be adequately protected by a minimum package, and which has a very long shelf life. These, and other objects and advantages of the invention, are realized by the provision of an electrode whose skin engaging surface is formed by a combination adhesive and electrolyte mixture performing the entire ionic transfer and adhesive function. In another form of the invention, the adhesive function is augmented or replaced by the use of a second adhesive material which is exposed at spaced points over the working surface of the electrode. The combined adhesive and electrolytic substance is formed by mixing a salt in an adhesive which includes, or has added to it, a solvent for the salt. In the preferred form, the adhesive in the mixture is water soluble. The primary solvent should have a low vapor pressure so that it does not evaporate away completely. If the adhesive is also water soluble, perspiration will not interfere with attachment of the electrode to the skin, and cleaning after removal of the electrode is simplified. The salt should include a metal salt and the adhesive-electrolyte, or some other part of the structure should include current collectors made of the same metal that is included in the salt. One advantage of the invention is that not all of the salt need be metal salt, and, to some extent, salt content can be reduced by the addition of current collecting metal. All that is required is to provide a reversible ion transfer path and that is done by including metal, salt of what should ordinarily be the same metal, and a solvent for the salt. The primary solvent should be one that will not evaporate completely so that the electrode is instantly operable. However, in many applications, instant operation is not required. The electrode will still be operative in a very short time if it becomes completely dry. It is customary to clean the skin area to which an electrode is applied, and that cleaning can be done with water or an aquaeous alcohol solution. If the electrode is applied to a skin area that has been so cleaned, the small amount of moisture that remains is entirely adequate to activate a previously dry electrode. Even if no water is added, perspiration issuing from under the electrode will render it operative in a matter of seconds.

In addition to the adhesive and salt mixture, some of the advantages and objects of the invention are provided by an electrode structure in which the adhesive and salt material is held in a pliant patch of material which has a foraminated, or a mesh, or screen form, or any other form which openings are provided in which adhesive salt mixture may be retained. The construction includes a metallic terminal. The terminal makes contact with the adhesive and salt mixture. An electrode of that construction need have a total area no larger than that of prior electrodes, but it forms an electrolyte to skin junction, having much greater contact area than previous electrodes. Since the area of electrical contact is greater, the concentration of salts may be far less with a consequent reduction in the amount of irritation and discomfort suffered by the patient. Irritation can be several orders of magnitude less. For example, the conventional electrode mentioned above has a diameter of 45 millimeters. The gel cavity is about 12 millimeters in diameter. The total area of skin covered is 1590 square millimeters. The area of the active surface is only 113 square millimeters. In an electrode according to the invention having 45 millimeter diameter, the entire area of 1590 square millimeters is active. Thus, in this example, an electrode made according to the invention has an active area about 14 times as great as the prior art electrode. That means that the electrode of the invention will exhibit a resistivity which is 10 to 14 times less than that of the prior electrode. Resistivity does not need to be reduced. Instead, the resistivity will remain the same if salt concentration is reduced from one-tenth to one-fourteenth that of the prior electrode whereby the degree of irritation is reduced by a similar factor. On the other hand, increased area makes it possible to select a metallic salt that exhibits very low irritation, notwithstanding that it exhibits somewhat higher resistance than the conventional materials, because that higher resistivity can be compensated for by the greater area.

IN THE DRAWINGS

Figure 1:
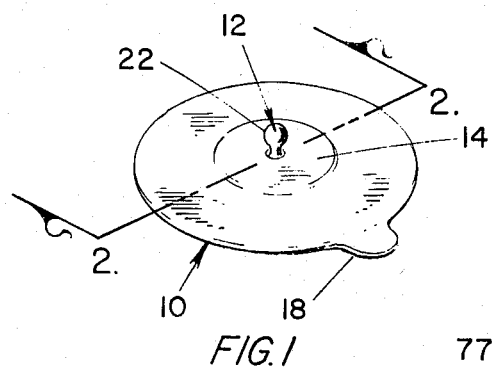
FIG. 1 is an isometric view of an electrode which embodies the invention.

In FIG. 1, the numeral 10 designates the electrode generally. It comprises a central button connector 12, which is surrounded by a stiffening disc 14. The disc overlies a circular, adhesive electrode pad 16. A semi-solid adhesive electrode paste is exposed at the bottom of the pad. To protect the paste, and to keep the surface clean, a protective covering overlies the bottom of the pad. The covering is generally circular in this embodiment, except that it has a peel-off tab 18, extending laterally to one side. The covering is made of a material which will adhere to the adhesive at the underside of the electrode pad, but which may be peeled away easily without disturbing the adhesive.

Figure 2:
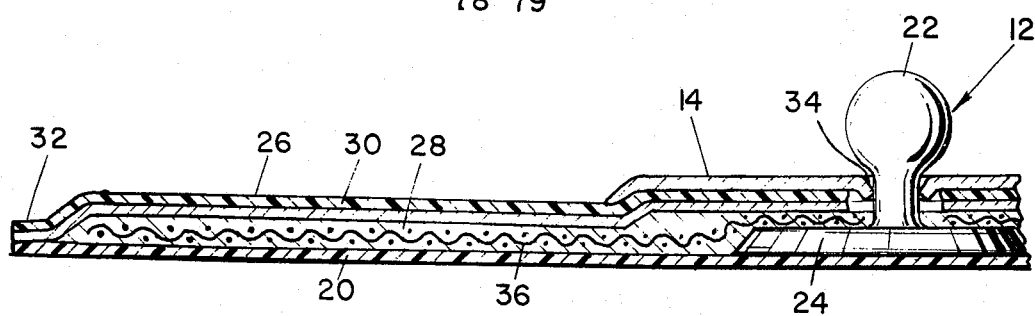
FIG. 2 is a view in central, vertical section taken on line 2—2 of FIG. 1.

The electrode is shown in cross-section in FIG. 2. Except for the tab 18 of the lower covering 20, the unit is symetrical about its central axis, so it is necessary to show only little more than half of the unit to show all of its features. In this embodiment, the connector 12 is shaped like the male portion of a snap fastener. The snap fastener is preferred, although the female portion could be included in the electrode rather than the male portion. Of course, other connector forms could be used.

The connector, in this case the stud 22, must be electrically conductive. It can be made of metal. However, in this embodiment, it is made of plastic, the outer surface of which has been metallized by a vacuum deposition process. Any other process may be employed that will result in a coating, both of the male portion of the connector and of its circular skirt 24. The connector, being circular, is not cross-sectioned in FIG. 2. The coating thickness must be sufficient so that a good electrically conductive path is formed between the surfaces of the stud and the upper face of the skirt 22. In this embodiment, all surfaces of the connector are metallized.

The function of the electrolyte is to complete a reversible ionic path from the subject to the metal connector. That can be accomplished by physically bridging the space from the subject to the connector with ions and a medium in which those ions are mobile. That is accomplished by bridging the space with a solvent in which a salt is dissolved. To avoid development of variable potentials across the solvent, the salt is, in whole or in part, the salt of the same metal that forms the surface of the connector. The resistivity of the path and its stability is enhanced by keeping the path short and by providing parallel paths. That can be accomplished by the inclusion of powders of the same metal in the electrolyte and/or by providing a metal or metallized screen in, or on, which the electrolyte is carried. The provision of such a structure is one of the features of the invention and of this embodiment.

The fact that the salt must be in solution presents three mechanical problems. First, it is necessary to retain the solvent so that it can be brought into contact with the subject at the desired place. Second, it must be held in contact at that place for a protracted period. Third, it must not evaporate away. In the prior art electrode, mentioned above, the solution to those problems is to contain an electrolyte filled sponge in a cup which is taped, open side down, on the patient's skin. The sponge more than fills the cup when relaxed, so a large area tape is employed. To prevent evaporation, electrodes are contained in hermetically sealed packages until used.

The invention provides two answers to these mechanical problems, and the two answers are complementary so that both answers can be employed in the same electrode. In one answer, the solvent is contained in and is a part of an adhesive material. The solvent is combined with the salt simply by mixing the salt in the adhesive. The resulting mixture serves both as the electrolyte and as the means for making the electrolyte adhere to the subject and to the metal connector. In the other answer to the mechanical problems, the solvent, or carrier, is mixed with the salt and some vehicle to form a paste. A pliant, foraminated screen, or grid, or open call plastic sheet, or non-woven cellular fabric, or some other kind of patch which is formed with openings, is impregnated with the paste. One side of the patch is coated with adhesive so the adhesive appears as islands in an electrolyte paste surface. Those islands of adhesive are adhesively bonded to the subject by pressing the patch to the subject's skin whereby the electrolyte paste is maintained in contact with the skin.

These two answers to the mechanical problems are combined by substituting the solvent containing adhesive of the first answer for the electrode paste of the second. Thus, the solvent containing adhesive and salt mixture is used to impregnate the patch. The adhesive of the second answer may be omitted. However, it is preferred to retain both adhesives. The adhesive of the first answer is made water soluble and the adhesive of the second answer is not. Doing that provides a special advantage because it means that an electrode that has become dry can be quickly activated by the solvent used to cleanse the place where the electrode is applied, or by perspiration under the whole area of the electrode.

There are good solvents which cause little skin irritation, which have very low vapor pressure, and which are solvents, both for the electrolyte salt and for suitable adhesives. In fact, in some cases, the solvent is the adhesive. The invention employs such solvents. In the preferred embodiment, it employs solvents of that kind which are themselves soluble in water so that no problems will be created by perspiration or other application of water. Further, a water soluble solvent is employed so that the electrode will be activated by perspiration or other addition of water in the event that the primary solvent does evaporate away.

To facilitate discussion, the term "adhesive-electrolyte" means a mixture of adhesive and salt. The mixture also will contain a solvent as a component of the adhesive or as an added component, but the term denotes the mixture even if dried out.

In the electrode of FIGS. 1 and 2, the reference numeral 26 designates a thin, circular patch of plastic material. It has a central opening through which the stud 22 extends. The adhesive-electrolyte material is designated by the reference numeral 28. In this embodiment, to facilitate manufacture, a thin layer 30 of a second, water-impermeable adhesive is applied as a coating to the underside of the plastic patch 26. In the assembled electrode, that thin layer of adhesive 30 is adhesively bonded at its lower surface to the upper surface of the layer of adhesive-electrolyte material 28. The layer of material 28, underlies all but the outer peripheral margin 32 of the plastic patch 26. It overlies the upper surface of skirt 24 of connector 12 at the middle of the electrode. Material 28 forms an adhesive bond with the metal, or metallized surface, of the skirt 24. The area at the upper surface of the electrode around the central stud 22 is strengthened, and the contact between the material 28 and the skirt 24 is strengthened by the circular stiffening member 14 which is swaged at the periphery of 34 of its inner opening to the shank of the stud 22. The stiffener may be made of metal or plastic, although plastic is preferred.

In the embodiment of FIGS. 1 and 2, the adhesive-electrolyte material is applied as a coating to a second patch of pliant material which is formed with many openings which extend through the material or through which the electrolyte paste or adhesive-electrolyte can permeate. The adhesive-electrolyte material extends through those openings so that there is communication between the materials and the opposite side of the patch. The patch may be formed of a thin layer of cellular plastic material of the kind in which the cells are open. It may be formed of a woven or a non-woven fibrous material. It may be foraminated, or be formed as a grid. Those several forms are substantially equivalent, and for convenience, the term "foraminated" is used to designate any one, or all of them. A primary function is to serve as a holder, or retainer, for the adhesive-electrolyte material in the circumstance in which it is very dry or very wet.

For the sake of clarity, the foraminated patch of material is represented schematically as a grid in FIG. 2 where the section has been taken such that the ends of the grid elements that extend in one direction are visible. For identification, the reference numeral 36 designates the grid ends and the foraminated patch for which they are a part. That foraminated structure adds greatly to the mechanical integrity of the adhesive-electrolyte layer. It is necessary to include some metal of the same kind that forms the salt in the electrolyte to serve as current collectors. A convenient way to include that metal is to mix metal powder in the adhesive-electrolyte material and the material 28 does include metal powder.

Alternatively, the metal can be included as part of the pliant patch 36. The patch could be made of metal screening. In this case, the patch 36 is a plastic screen, the surface of which is metallized. In this case, the metal is zinc, the metal power is zinc, the metal on the surface of the connector is zinc, and the salt is zinc carbonate.

In addition to serving as an adhesive, the adhesive component in the adhesive-electrolyte material serves substantially the same function as does the gel in prior art electrodes. Thus, it serves as a filler in which the concentration of salt can be varied, and by which the salt is held dispersed more or less uniformly. It serves as the vehicle for containing or retaining the solvent so that it, too, will be dispersed relatively uniformly throughout the body of electrolyte.

The adhesive is a non-conductor of electricity, but the dissolved metal salts are ions and they and the metal powder are conductive. The resistivity exhibited by the electrode measured from its lower face to the connector varies with the proportion of salt and powdered metal to adhesive. The proportions are not critical, so long as ionic conductivity is maintained. Total resistance is lowered by increasing the area of contact between skin and the adhesive-electrolyte material. The increased area made possible by the invention permits a reduction in salt concentration and a consequent reduction in irritation.

Figure 3:
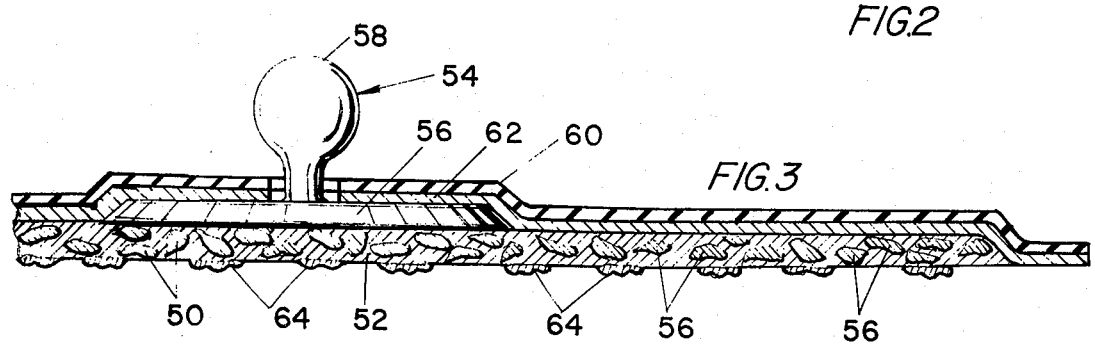
FIG. 3 is a view in central, vertical section of a portion of an electrode of alternative form.

FIG. 3 shows a central, sectional view of another form of electrode according to the invention. In this one, the foraminated patch is formed of a thin sheet of compressed non-woven, viscose fibers, which are held together by an adhesive. The adhesive is inert with respect to the electrochemical action of the electrode. Specifically, FIG. 3 attempts to depict a non-woven surgical tape as the foraminated patch. The cut end of the fibers are shown. Some of them are identified by the reference numeral 50. The patch is thoroughly impregnated with an adhesive-electrolyte material 52. That material contains a silver halide salt and powdered silver.

Before being impregnated with that material, one face, the lower face, of the surgical tape 50 is coated with a pressure sensitive adhesive material which is not water soluble. The coating is sufficiently thin so that the adhesive covers only the surface fibers. The tape is impregnated with the adhesive-electrolyte material by applying it to the opposite side of the tape, and then pressing to force it into the interstices between fibers. The material is forced through and appears at the opposite surface of the tape in the spaces between fibers. The effect is that the lower face of the electrode, the one that will make contact with the subject's skin, appears as a circular area of adhesive-electrolyte material which is studded with islands of non-water soluable adhesive. The area available for the electric junction between the electrolyte and the subject's skin is reduced in only small degree, but an electrode has been provided which will adhere to the skin in the presence of quantities of water sufficient to dissolve much of the soluble adhesive in the adhesive-electrolyte material. That kind of construction is an advantage when the patient is to be bathed without removing the electrode, and in a number of other circumstances.

In the embodiment of FIG. 3, the connector 54 has its skirt portion 56 lying above, and in contact with, the upper surface of the surgical tape 50, and the adhesive-electrolyte material 52 which it contains. The stud portion 58 of the connector extends through the central opening of a covering material 60 which is impervious to water. As in the case of FIGS. 1 and 2, the covering 60 has a layer of water insoluble adhesive 62 applied to its undersurface. In the finished construction, that layer of adhesive 62 bonds the covering 60 to the upper surface of the connector skirt 56 and it bonds the covering to the upper surface of the surgical tape 50. While the electrode is being stored, its lower face is covered with a sheet of easily removable protective material corresponding to the protective material 20 of FIG. 2. It has been omitted from FIG. 3 for the sake of clarity, so that the islands 64 of non-soluble adhesive at the lower face of the electrode can be more easily depicted and distinguished.

Figure 4:
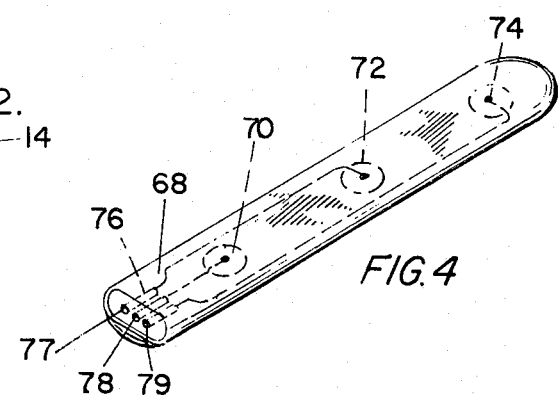
FIG. 4 is an isometric view of another alternative form of the invention.
Figure 5:
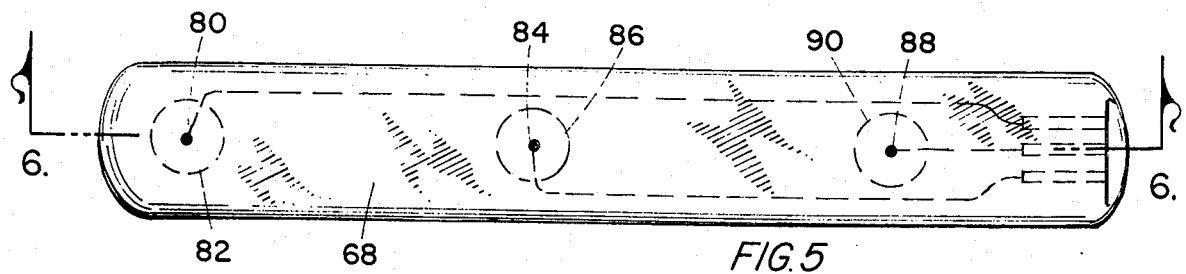
FIG. 5 is a top view of the electrode shown in FIG. 4 in which dashed lines illustrate the path of hidden conductors.
Figure 6:
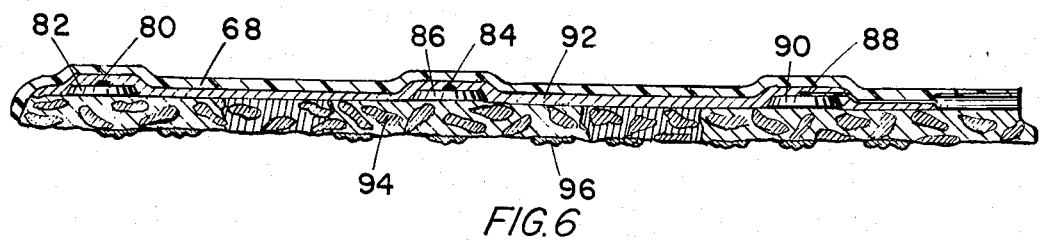
FIG. 6 is a cross-sectional view taken on line 6—6 of FIG. 5.

A third embodiment of the invention is shown in FIGS. 4, 5 and 6. Here, three electrodes are included in one structure to facilitate the taking of electro-cardiograms. Referring to FIG. 4, the three electrodes are contained in an elongated structure, the upper covering of which is impervious to moisture and which is formed with three spaced upwardly projecting areas 70, 72 and 74, in which the respective connectors are housed. At one end, the unit has a terminal housing 76 molded as an integral part of the cover. Three sockets 77, 78 and 79 are inserted in respectively associated openings in that terminal housing. They are electrically connected to small conductor wires that are embedded in the molded cover. The dashed lines in FIG. 5 illustrate the route followed by those conductor wires. Because they are embedded in the cover 60, the wires are not visible in any of the figures except FIG. 6 where their ends are shown to be bonded to respectively associated ones of three metal connector discs. Wire 80 is connected to disc 82. Wire 84 is bonded to disc 86, and wire 88 is bonded to disc 90. The underside of the molded cover 68 is covered with a layer of non-water soluble adhesive 92, and the upper faces of discs 82, 86 and 90 are adhesively bonded to that layer.

Both the molded cover and the adhesive layer 92 are electrically non-conductive. A length of surgical tape has one side pressed into contact with the adhesive layer 92. In this case, the wires 80, 84 and 88 are formed of any conductive metal. Discs 82, 86 and 90 are formed of silver or zinc. Below each metal disc, the non-conductive surgical tape is thoroughly impregnated with a material which includes a silver halide salt or zinc carbonate. That salt is contained in a water soluble binder, which, in the case of the material below discs 82 and 90, is not adhesive. It does include silver or zinc powder. On the other hand, to improve overall electrical characteristics, the binder under the central disc 86 is a water soluble adhesive. It, too, contains silver or zinc powder. In this case, the metal is silver.

The material under disc 82 is electrically insulated from the material under disc 86 because, in the region between them, the surgical tape is impreganted with a quantity of the same non-conductive adhesive material that is used to form the adhesive layer 92. The region in which that separating quantity of adhesive appears is identified by the reference numeral 94 in FIG. 6. Similarily, the electrolyte under disc 86 is electrically insulated from the electrolyte under disc 90 by a quantity 96 of that same non-conductive adhesive. The adhesive impregnates the surgical tape entirely across the width of the electrode structure and entirely through the thickness of the surgical tape.

The metal in the salt, in the metal powders that are dispersed in the electrolyte, and the metal of the conductors may be any of the metals that are customarily used in reference electrodes and in bioelectrodes. Silver is a good choice, and in that case, the salt would be a halide of the silver. The standard salt is AgCl. One of the advantages of the invention is that, because of the large contact area and consequent low resistance, some of the materials that ordinarily are not selected because of high resistivity, are excellent choices for this electrode. That is particularly true of the combination zinc and zinc carbonate, and zinc and zinc citrate. The salts, zinc carbonate and zinc citrate, are less an irritant than the conventional salts. One of the advantages of this invention is that it can use the zinc-zinc carbonate and the zinc-zinc citrate combination.

Many adhesives are suitable and their selection is well within the skill of the adhesive technologist. To preserve a semi-solid character, a humectant, or vapor pressure suppressant, is included. In the case of some adhesives, it is advantageous to include a small quantity of mold inhibitor, but that, too, is part of standard adhesive technology. By way of example, some suitable adhesive bases are poly-acrylamide, poly-vinyl-pyrolidone, poly-vinyl alcohol, poly-vinyl-pyridines, and cellulose derivitives.

Although I have shown and described certain specific embodiments of my invention, I am fully aware that many modifications thereof are possible. My invention, therefore, is not to be restricted except insofar as is necessitated by the prior art.

I claim:

1. An electrode for use in measuring bio-electric events comprising, in combination:
   a pliant patch of foraminated material;
   a quantity sufficient to measure bioelectric events of metal salt impregnating said patch of material;
   a connector having a surface formed of the metal of said metal salt in contact with said quantity of salt; and
   a quantity of adhesive covering one side of said patch adapted to be placed upon the skin.

2. The invention defined in claim 1 in which said quantity of salt is contained in a water soluble adhesive to form an adhesive-electrolyte.

3. The invention defined in claim 2 in which said pliant patch includes a screen comprising said given metal, the screen being in contact with said adhesive-electrolyte.

4. The invention defined in claim 2 in which said patch comprises a layer of non-woven viscous fabric.

5. The invention defined in claim 4 in which said metal is silver and said salt comprises a silver halide.

6. The invention defined in claim 4 in which said metal is zinc and said salt comprises zinc carbonate.

7. The invention defined in claim 4 in which said electrode further comprises a backing layer of water impervious, pliant covering material overlying covering and adhesively bonded to said pliant patch and to said connector at the side of said patch opposite said quantity of adhesive.

8. An electrode for use in measuring bio-electric events comprising in combination:
   a connector having a metal surface;
   a quanity of adhesive-electroylte material in physical contact with said metal surface;
   said adhesive-electrolyte material comprising the salt of the metal on the surface of said connector and in a quantity sufficient to measure bio-electric events; and
   said adhesive-electrolyte material further comprising powders of said metal.

9. The invention defined in claim 8 which further comprises a first pliant patch formed of a foraminated material impregnated with said quantity of adhesive-electrolyte material.

10. The invention defined in claim 9 which further comprises a protective patch formed of pliant, water impermeable material, said patch being protective adhesively bonded to one side of said first pliant patch.

11. The invention defined in claim 10 in which a surface of said first pliant patch comprises said given metal.

12. The invention defined in claim 11 in which said connector comprises a disc having one of its surfaces in engagement with the first pliant patch and said quantity of adhesive-electrolyte material.

13. The invention defined in claim 12 in which the other surface of said disc is adhesively bonded to said protective patch.

14. The invention defined in claim 13 in which surface areas of the side of said first pliant patch which faces away from said protective patch are covered with an adhesive which is substantially insoluble in water.

* * * * *